United States Patent [19]

Thomson et al.

[11] Patent Number: 4,798,790

[45] Date of Patent: Jan. 17, 1989

[54] MONOCLONAL ANTIBODY SPECIFIC FOR A PIGMENTATION ASSOCIATED ANTIGEN

[75] Inventors: Timothy M. Thomson, New York; M. Jules Mattes, Flushing; Lloyd J. Old, New York; Kenneth O. Lloyd, Bronx, all of N.Y.; Linda Roux, San Diego, Calif.

[73] Assignee: Sloan-Kettering Institute, New York, N.Y.

[21] Appl. No.: 756,362

[22] Filed: Jul. 18, 1985

[51] Int. Cl.$^4$ .................. G01N 33/53; G01N 33/577; C12N 5/00; A61K 39/00

[52] U.S. Cl. ..................................... 435/7; 435/172.2; 435/240.27; 436/536; 436/548; 436/813; 530/387; 530/808; 935/108; 935/110

[58] Field of Search ............... 435/29, 68, 7, 240.27, 435/948, 172.2; 436/548, 536, 811, 804, 813; 530/387, 808, 809; 935/103, 105, 110, 108

[56] References Cited

U.S. PATENT DOCUMENTS 4,591,572  5/1986  Mattes et al. .................. 436/811

OTHER PUBLICATIONS

Mattes et al., Int. J. Cancer, vol. 32, 1983, pp. 717–721.
Thomson et al., The Journal Of Investigative Dermatology, vol. 85, 1985, pp. 169–174.

*Primary Examiner*—Robert J. Warden
*Assistant Examiner*—Florina B. Hoffer
*Attorney, Agent, or Firm*—John P. White

[57] ABSTRACT

Monoclonal antibody TA99, which specifically binds to a pigmentation associated antigen present on melanoma cells is described. Additionally, the hybridoma cell line deposited with the ATCC under Accession Number HB 8704 from which the antibody is derived, as well as methods for using the antibody are described.

9 Claims, 5 Drawing Sheets

MONOCLONAL ANTIBODY SPECIFIC FOR A PIGMENTATION ASSOCIATED ANTIGEN

FIELD OF THE INVENTION

This invention relates to the field of cancer immunology. More specifically, it relates to monoclonal antibodies which are specific to cancer associated antigens, the hybridoma cell lines which produce the antibodies, and use of the antibodies.

PRIOR ART

The pigmentation associated antigen to which the monoclonal antibody disclosed and claimed herein is specific is described in co-pending U.S. patent application Ser. No. 481,379; the disclosure of which is incorporated by reference. See also Mattes, et al., Int. J. Cancer 32:717–721 (1983); which shows that this antigen is not tumor restricted. The antigen differs from other melanocyte differentiation antigens, as described by Watanabe, et al., J. Exp. Med. 156:1884–1889 (1982); Hersey, et al., Brit. J. Cancer 40:615–624 (1979); Leong, et al., J. Surg. Res. 24:245–252 (1978); Gupta, et al., J. Natl. Cancer Inst. 70:83–92 (1984); Naughton, et al., J. Exp. Med., 158:246–251 (1983); Houghton, et al., PNAS USA 77:4260–4264 (1980). The antigen is, however, identical to the gp75 antigen described by Tai, et al., Cancer Res. 43: 2773–2779 (1983), and is distinct from melanin and from tyronase. Hearing, et al., Cancer Res. 37:1519–1524 (1977), describe a gp70 melanosomal protein, but work by Hearing has shown that this protein does not react with monoclonal antibody TA99. Heany-Kierds, et al., Cancer Res. 42:2310–2316 (1982), describe a gp75 melanoma antigen, but this is not pigmentation-associated.

As will be seen, there is an extensive literature on melanoma-associated antigens. There is no teaching in the art, however, of monoclonal antibodies which are specific to the pigmentation associated antigen gp70-80, with an isoelectric point of about 5.2-5.6, described by Mattes et al., supra. A monoclonal antibody which is specific to this antigen is the subject of this invention.

BACKGROUND

Pigmented melanoma cells and cultured melanocytes express a differentiation-related glycoprotein weighing about 70-80 kilodaltons, and having an isoelectric point of about 5.2-5.6. Mattes, supra. The antigen is referred to as a pigmentation associated antigen, or "PAA." The antigen was identified previously by precipitating polyclonal antibodies from sera of a melanoma patient. The antibodies thus precipitated reacted with autologous tumor cells, pigmented melanoma cells, and with normal melanocytes. There was not reaction with non-pigmented melanomas or other types of malignant or normal cells.

Based upon the earlier work described, a murine monoclonal antibody has now been produced which is specific to pigmentation associated antigen gp70-80. The production of this monoclonal antibody, and its use to examine more extensively distribution and characteristics of pigmentation associated antigen are described.

DETAILED DESCRIPTION OF PREFERRED EMBODIMENTS

Figure 1:
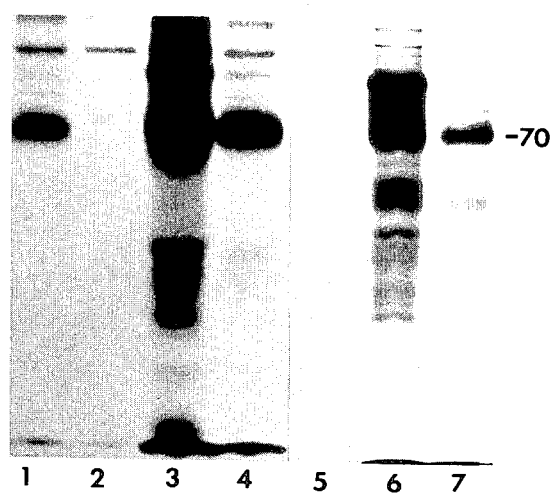
FIG. 1 is an audiogram of immunoprecipitates obtained using cell line SK-MEL 23 labeled with $^{125}I$ (lanes 1-4, 1 day exposure), or $^{35}S$ methionine (lanes 5-7, 2 month exposure), using acrylamide gel electrophoresis.

Hybridoma cell lines which are described in this application and which produce the monoclonal antibody TA99 have been deposited with the American Type Culture Collection, Bethesda, Md. and carry the designation HB 8704.

Cell Lines and Tissues

The tumor cell lines employed are listed in Table I, and were cultured as described by Mattes et al.; Int. J. Cancer 32:717–721 (1983). Mouse myeloma NS-1 cells were maintained as described by Mattes, et al., Hybridoma 2:253–264 (1983). Normal human tissues for immunoperoxidase studies were frozen in liquid nitrogen and kept at −70° C.

Sera

Sera, as characterized by Mattes, et al., Int. J. Cancer 32:717–721 (1983) were used. Mice were immunized with cell lines by intraperitoneal injection of approximately $10^7$ cells, which had been scraped from tissue culture flasks and washed 2 times with Dulbecco's phosphate-buffered saline (DPBS, GIBCO, Grand Island, NY). Two to four injections were given at 2 week intervals. A rabbit antiserum to purified hamster tyrosinase, which cross-reacts with human tyrosinase as described by Halaban, et al., J. Cell Biol 97:480–488 (1983) was used. Mouse antisera reacting with tyrosinase were obtained by immunizing mice with solubilized crude melanosome preparations, which are described infra. Approximately 0.3 mg of protein was emulsified with complete Freund's adjuvant and injected subcutaneously. Two months later mice were boosted similarly except with incomplete Freund's adjuvant.

Monoclonal Antibody Production

Spleen cells from an immunized mouse known to be producing antibodies to pigmentation associated antigen were fused with NS-1 cells with polyethylene glycol as described by Dippold, et al., PNAS USA 77:6114–6118 (1980). After the fusion, cells were plated into 20 24-well Costar 3424 plates (Costar, Cambridge, MA) and culture supernatants were screened for anti-pigmentation associated antigen antibodies by immunoprecipitation as described infra. Cloning was performed by limiting dilution in 96-well Costar 3596 plates. Hybridomas were subsequently grown in nu/nu mice and serum obtained as described previously by Dippold, et al., supra.

Radiolabelling $^{125}$I-labeling of detergent-solubilized cell extracts as described by Mattes, et al., Int. J. Cancer 32:717–721 (1983) was used. Metabolic labeling with [$^{35}$S]-methionine as described by Cairncross, et al., PNAS USA 79:5641–5645 (1982) or [$^3$H]-glucosamine as described by Ogata, et al., PNAS 78:770–774 (1981) and Con A-Sepharose fractionation of labeled extracts, as per Mattes, et al., Hybridoma 2:253–264 (1983) were used. For labeling with [$^3$H]-tyrosine, cells were incubated for 16 hr. with 0.5 mCi [$^3$H]-tyrosine (54.6 Ci/mmole, New England Nuclear, Boston MA) in tyrosine-free medium supplemented with 5% dialyzed fetal calf serum (FCS).

Immunoprecipitation

Immunoprecipitation of $^{125}$I-labeled samples was carried out as described in Mattes, et al., Int. J. Cancer 32:717–721 (1983). Immunoprecipitation of metabolically labeled samples was performed in similar fashion and has been described by Mattes, et al., Hybridoma 2:253–264 (1983). Gels with $^{125}$I-labeled samples were dried and exposed to Kodak XAR film at −70° C., using an intensifying screen (Dupont Lightning Plus). Gels with metabolically labeled samples were processed for fluorography, as described by Ogata, supra. Two-dimensional gel electrophoresis was performed following O'Farrell and O'Farrell, *Methods in Cell Biology*, v. 16, pp. 407–420 (1977).

For sequential immunoprecipitation, the first precipitation was as described except that pelleted SA was mixed with the sample, to avoid dilution. After centrifugation, pellets were discarded, and the supernatant were incubated with the second mouse antibody and rabbit anti-mouse IgG. After 4 hours, SA was added, and subsequent procedures were followed as described, supra. For inhibition of immunoprecipitation, cells to be tested were scraped from 75 cm$^2$ flasks, washed three times with PBS, pelleted, and extracted with 4 pellet volumes of lysis buffer as described above. Extracts were either used immediately or frozen at −20° C. Extracts were incubated overnight at 4° C. with 0.5 ml of diluted hybridoma supernatant. SA-precleared $^{125}$I-labeled samples (10$^5$ cpm), of a Con A eluate fraction from SK-MEL-23, were added and the mixture was incubated for 1 hour. Rabbit anti-mouse IgG (0.015 ml) was added, and after two hours 0.015 ml SA suspension was added, and processed as described above. A solubilized membrane fraction of SK-MEL-23 was prepared as described by Mattes, et al., Hybridoma 2:253–264 (1983).

Serological Assays on Cell Lines and Tissues

Cell lines were grown in Falcon 3034 microtest plates. The rosetting assay for cell surface antigens has been described by Mattes, et al., supra. To detect intracellular antigens, plates were washed three times with DPBS and fixed for 45 minutes with 2% buffered formaldehyde using the method of Farr, et al., J. Immunol. Meth. 47:129–144 (1981). Plates were then washed 3 times with DPBS, incubated for 30 minutes with 0.05% NP40 in PBS, and washed two times with PBS containing 5% FCS. Antibody (0.01 ml) was added to each well, and incubated for one hour at room temperature. Plates were washed two times with PBS, 5% FCS, and wells were incubated for one hour with 0.01 ml of peroxidase-conjugated rabbit anti-mouse IgG (DAKO, Accurate Chemicals, Westbury, NY) diluted 1:50 in PBS. Plates were washed two times with PBS, and incubated with the substrate 3-amino-9-ethyl carbazole (Sigma) [9]in 0.01 ml for 15 minutes, then washed two times with PBS and once with distilled water. Immunofluorescence on cell lines was performed similarly, using fluorescein-conjugated goat anti-mouse Ig (Cappel) at a 1:40 dilution. Observation was with a Leitz Orthoplan microscope, using a 100W mercury lamp and filter cube 12. Tissue sections were stained by immunoperoxidase, using 0.005 nm cryostat sections. Mattes, et al., Hybridoma, supra.

Melanosome Preparation and Assays for Tyrosinase and Melanin

An enriched preparation of melanosomes was obtained from spent medium of cultures of a highly pigmented melanoma cell line (SK-MEL-173). After discarding a low speed pellet (10 min, 600 g), melanosomes were pelleted by centrifugation at 100,000 g for 30 minutes. The enrichment of melanosomes in these samples was confirmed by electron microscopy. The melanosome preparations were extracted with 0.1% deoxycholate, 0.1M Tris HCl, pH 7.4, 1 mM PMSF and 20 U/ml Aprotinin (Sigma). Insoluble material was removed by centrifugation (100,000 g for 30 min) and the extract was assayed for tyrosinase activity.

Enzyme activity was determined by a modification of the $^3$H H$_2$O-release assay described by Pomerantz and Li, Meth. Enzymol. 17A:620–626 (1970). Samples were incubated with 0.15 ml reaction mixture containing 1 mM L-tyrosine, 0.1 mM L-DOPA, 1.25 $\mu$C.i (3,5)-[$^3$H]-tyrosine, 0.1 mg/ml gelatin, 0.1M Na phosphate pH 7.3. After 20 minutes at 37° C., the reaction was terminated by transferring tubes to ice followed by addition of 0.8 ml 0.1N HCl and 200 mg charcoal. Tubes were allowed to stand at room temperature for 1.5 hour with occasional mixing, then centrifuged at 1000 rpm for 10 minutes, and 0.10 ml of the supernatant was counted in 10 ml Liquiscint (National Diagnostics, Somerville, N.J.). Radioactivity in negative control tubes containing buffer was subtracted from sample counts. To detect antibodies to tyrosinase, a solubilized melanosome extract containing a known amount of enzyme activity was incubated with varying amounts of mouse or rabbit serum or Ab TA99 plus 0.015 ml of rabbit antiserum to mouse IgG (Cappel). After overnight incubation at 4°, 0.015 ml packed SA was added in 0.015 ml, incubated 1 hour at 4°, and centrifuged at 600 g for 10 minutes. Residual enzyme activity in the supernatants as well as immunoprecipitated enzyme activity in the pellets were assayed.

RESULTS

Production of a Monoclonal Antibody to PAA

In preliminary experiments sera from mice immunized with whole cells of a darkly pigmented melanoma (SK-MEL-23) were tested for immunoprecipating activity after absorption of such antisera with cells of a non-pigmented melanoma (SK-MEL-37). Remarkably, the sera were essentially specific for pigmentation associated antigen (FIG. 1). Such reactivity was observed consistently in sera from mice immunized with several different pigmented melanoma cell lines, and was not seen in sera from mice immunized with non-pigmented melanomas or carcinomas.

The identity of the component precipitated with pigmentation associated antigen with is defined by precipitation by human serum was established in several ways. The Mr 70,000 component was precipitated by the absorbed mouse antisera only from pigmented melanoma cell lines. Sequential immunoprecipitation experiments demonstrated that pigmentation associated antigen was precipitated by the absorbed mouse antisera, since preclearing antigen preparations with the mouse antisera removed the antigen recognized by human serum (not shown, but see FIG. 2 for a similar experiment with TA99). The absorbed mouse sera precipitated a much stronger band than human serum, using $^{125}$I-labeled extract as described supra. It also precipitated a similar component after labeling cells with [$^{35}$S]-methionine (FIG. 1), which is not seen with human serum, presumably because the band is too faint to be apparent above the background.

The reason that antibodies to pigmentation associated antigen were so readily detected is not fully understood, but several factors are involved. PAA appears to be a fairly abundant cellular component, since in an $^{125}$I-labeled antigen preparation it was one of the major proteins detected, as described infra. Also, since the $^{125}$I-labeled antigen preparation was a Con A eluate fraction, antibodies to components not binding Con A would not be detected.

Based on these results, an experiment was devised to attempt to select pigmentation associated antigen-specific monoclonal antibodies from a fusion using a mouse immunized with whole SK-MEL-23 cells. Supernatants from wells containing visible colonies were screened by immunoprecipitation of $^{125}$I-labeled extracts from SK-MEL-23 and SK-MEL-37, a non-pigmented melanoma. Supernatants precipitating significantly more counts from SK-MEL-23 than from SK-MEL-37 were subsequently retested and the immunoprecipitates analyzed by PAGE. Three supernatants of 293 tested precipitated a component of Mr 70,000 from SK-MEL-23 but not from SK-MEL-37 cell extracts. After cloning only one hybridoma continued to produce a specific antibody, TA99, an IgG2a. Monoclonal antibody TA99 is an extremely potent precipitating antibody since strong bands, seen after a 5 day film exposure, were precipitated by 100 nl of hybridoma tissue culture supernatant or by 0.5 nl of serum from nude mice bearing the hybridoma. The selection of such a strong precipitating antibody is probably due to the fact that the initial screening was done by immunoprecipitation. Only one other antibody, of many tested in this laboratory to various antigens precipitates strongly at such low concentrations, and this also was selected initially by immunoprecipitation.

Figure 2:
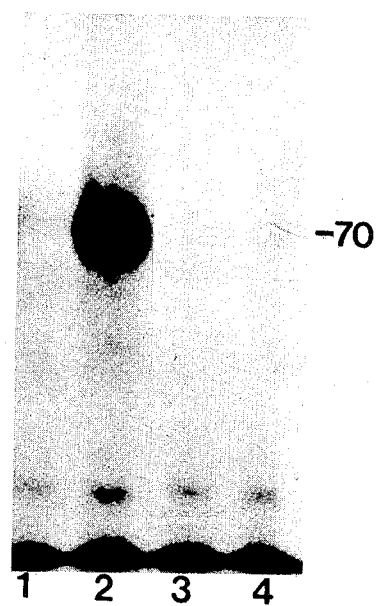
FIG. 2 shows precipitation of pigmentation associated antigen using monoclonal antibody TA99. The audiogram shows analysis by acrylamide gel electrophoresis of $^{125}I$ labeled SK-MEL 23 immunoprecipitates.

The TA99 antigen was shown to be identical to pigmentation associated antigen recognized by human serum by sequential immunoprecipitation. TA99 completely removed from $^{125}$I-labeled SK-MEL-23 extracts the molecules precipitable by AU serum. Pre-clearing with an unrelated mouse monoclonal antibody of the same subclass had no effect on the immunoprecipitation of PAA by human serum (FIG. 2). Human serum is relatively weak in precipitation and does not effectively remove its own antigen in sequential precipitation experiments, so the reverse sequential precipitation could not be done. It is therefore possible that human serum reacts with only a fraction of molecules precipitated by antibody TA99. The data described and other data presented below strongly indicate that the TA99 antigen is identical to pigmentation associated antigen.

Distribution of PAA

The distribution of pigmentation associated antigen in cell lines of various types and in frozen sections of normal tissues was investigated. Previous data with human serum indicated that pigmentation associated antigen expression was correlated with pigmentation of cell lines Mattes, et al., Int. J. Cancer 32:717–721 (1983). Tissue sections could not be examined with human serum due to the presence of many other antibodies in the serum.

Using sensitive rosetting assays designed to detect cell surface antigens, Ab TA99 did not react with cultured SK-MEL-23 cells. It was concluded that, as was suggested by previous studies in Mattes, supra, that pigmentation associated antigen is not located on the cell surface. Immonofluorescence and immunoperoxidase staining of pigmented melanoma cells, fixed with formaldehyde and permeabilized with detergent, showed reactivity of TA99 with intracellular components having a perinuclear localization. No reactivity was observed with non-pigmented melanoma cells or non-melanoma cells. The distribution of pigmentation associated antigen within the cell was identical with the distribution of melanosomes, suggesting that pigmentation associated antigens might be a melanosomal antigen. However, this localization interfered somewhat with observation, since the melanin in highly pigmented melanomas is so dense that it partially obscures staining by either immunofluorescence or immunoperoxidase.

In order to screen a large panel of cell lines for reactivity with Ab TA99, an assay based on inhibition of immunoprecipitation of labeled SK-MEL-23 with unlabeled detergent-solubilized cell extracts was developed. Sixty-eight tissue culture cell lines, including melanomas, astrocytomas, carcinomas, lymphomas and leukemias were examined. Positive extracts were tested at serial 2-fold dilutions to allow an estimate of an amount of antigen activity (Table I). Audioradiographs of gels from a similar PAA precipitation inhibition assay using human serum were shown previously by Mattes, et al., Int. J. Cancer 32:717–721 (1983). Only extracts from pigmented melanoma cells inhibited the reactivity of Ab TA99. The relative amount of antigen in these cells was correlated without exception with a visual estimate of the degree of pigmentation of cell pellets. Melanin was not quantitated because four procedures for melanin quantitation tested (Halaban et al., supra, Whittaker et al., Dev. Biol. 8:99–127 (1963); Meyshens, et al., Cancer Res. 40:2194–2196 (1980); Oskawa et al., Yale J. Biol. Med. 46:500–507), produced only partial solubilization of the melanin in highly pigmented melanomas.

The intracellular location of pigmentation associated antigen was investigated in several preliminary experiments. A membrane preparation was as active as whole cells in the inhibition assay, indicated that most or all of the antigen is membrane-bound. Melanosome preparations were obtained from both disrupted cells and from spent medium. These were active in the inhibition assay, both with and without detergent solubilization. These data are consistent with the possibility that the antigen is a melanosome antigen, but tests with a more rigorously purified melanosome preparation, or immunoelectron microscopy, will be required to confirm this.

Figure 3:
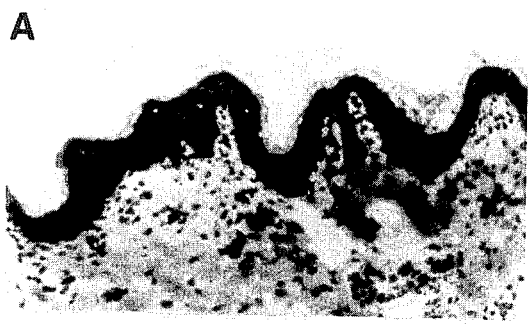
FIG. 3 shows reaction of monoclonal antibody TA99 with basal layer of epidermis, in photographs of 5 μm cryostat sections of normal Caucasian foreskin stained with one of (A) hematoxylin; (B) immunoperoxidase with antibody MG144, used as a control IgG; or (C) immunoperoxidase with TA99.
Figure 3:
Figure 3:
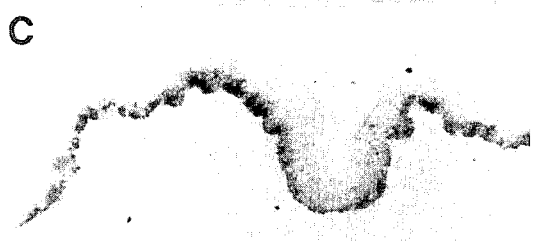

In frozen sections of 19 normal human tissues tested, Ab TA99 reacted only with the basal layer of the epidermis (FIG. 3) and the pigmented cells of the eye, including both the choroid and the pigmented retinal epithelium. The substantial nigra was also examined, but results were inconclusive since the melanin was so dense that superimposed peroxidase staining would have been difficult to detect. In the epidermis since the epithelial cells of the basal layer were stained, it is concluded that the antigen is probably transferred to these cells together with melanosomes from melanocytes; melanosomes also are highly concentrated in the basal layer. Negro skin was more darkly stained by TA99 than Caucasian skin, paralleling the density of melanosomes, though the dense melanin in Negro skin partially obscured the immunoperoxidase staining. Other tissues examined that were negative for TA99 included the thyroid, testes, kidney, liver, pancreas, colon, brain, spleen, thymus, uterus, ovary, lung and lymph node.

Biochemical Characteristics of Pigmentation Associated Antigen

Monoclonal antibody TA99 immunoprecipitated a Mr 70,000 molecule from SK-MEL-23 cells metabolically labeled with [$^{35}$S]-methionine, [$^{3}$H]-tyrosine, [$^{3}$H]-glucosamine or [$^{3}$H]-fucose, in addition to standard $^{125}$I-labeled cell extract. The Mr estimate of the antigen varied in the course of our experiments; in earlier experiments it was calculated to be 70.000; Mattes, supra, while in later experiments it was calculated to be 75–80,000. It is suspected that unknown variation in acrylamide gel composition caused the glycoprotein antigen to migrate differently relative to the nonglucosylated molecular weight standards bovine albumin and phosphorylase. See, e.g., Segrest, et al., Meth. Enzymol. 28B:54–63 (1972). Two dimensional analysis of immunoprecipitated PAA labeled with each of three isotopes demonstrated an isoelectric point in the pH range 5.2–5.6. Data indicate that the pigmentation associated antigen is a fairly abundant molecule in pigmented melanomas. In the Con-A-Sepharose eluated fraction of cell extracts, after labeling with $^{125}$I, this antigen was one of the major spots visible in two-dimensional PAGE. This was demonstrated by pre-clearing cell extracts with Ab TA99, to selectively remove PAA, before applying to the gel (not shown).

Figure 4:
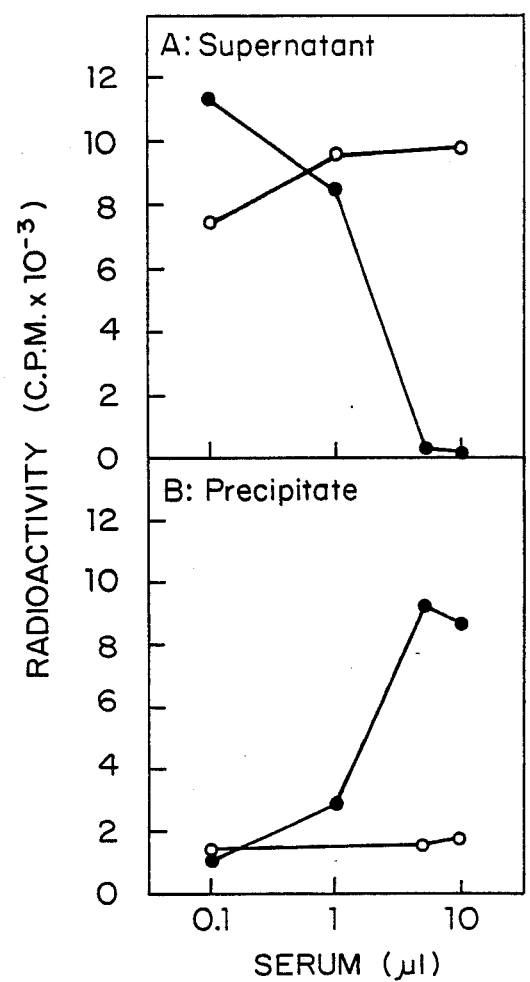
FIG. 4 shows experimental results proving pigmentation associated antigen is not tyrosinase. Extracts of SK-MEL-173 were incubated with dilutions of mouse-antihuman tyrosinase antiserum, or monoclonal antibody TA99, and were followed by rabbit anti-mouse IgG. Following pelleting, supernatant and pellet were assayed for tyrosinase activity. The ordinate represents $^3H$ released from $^3H$ tyrosine.

Two other markers of pigmented cells, tyrosinase as described by Dippold et al., supra, and Nishioka, et al., Eur. J. Biochem. 85:137–146 (1978) and gp75 as described by Tai, et al., Cancer Res. 43:2773–2779 (1983), are similar in many respects to pigmentation associated antigen, and it was determined that they are not identical. Ab TA99 had no activity in an immunoprecipitating assay designed to detect anti-tyrosinase antibodies (FIG. 4). Two antisera to human tyrosinase were active as positive controls in these assays; they were able to immunoprecipitate tyrosinase activity whereas TA99 was not.

Figure 5:
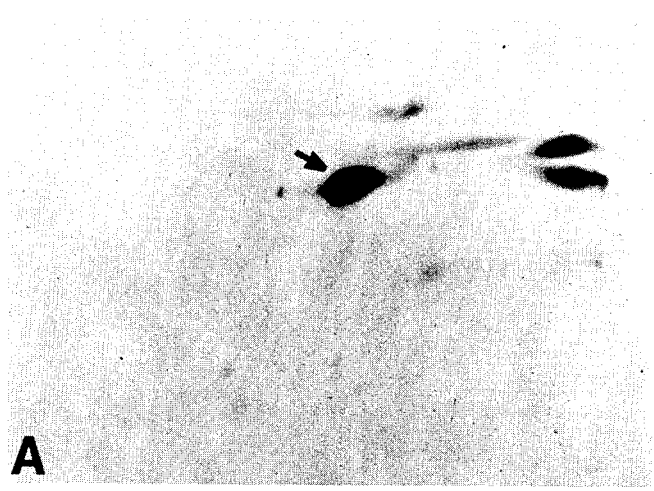
FIG. 5 shows audiograms of 2-dimensional gels of $^3H$-glucosamine-labeled SK-MEL-23, showing identity of pigmentation associated antigen with gp75. For details of the experiments showing this, see the following Description of Preferred Embodiments.
Figure 5:

Gp75 was identified in other studies, e.g., Tai et al., supra as a major component of extracts of melanoma cell lines labeled with [$^{3}$]-glucosamine and ib quantity was correlated with degree of pigmentation. To determine whether it was identical to pigmentation associated antigen, pre-cleaning experiments were performed with monoclonal antibody TA99 to remove pigmentation associated antigen. The remaining supernatant was examined by 2-dimensional PAGE, which allows the identification of gp75. As will be seen from FIG. 5, this pretreatment removed nearly all of the gp75 from the sample. Therefore, it can be concluded that the gp75 antigen described by Tai, supra, is identical to the gp70–80 antigen described herein and monoclonal antibody TA99 specifically binds thereto.

Copending U.S. application Ser. No. 481,379 describes a differentiation antigen characteristic of pigmented cells. This application describes a monoclonal antibody, TA99, which specifically reacts thereto, as well as methods for obtaining and using both the hybridoma cell line and the antibody thus produced.

While there have been described what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. A hybridoma cell line designated TA99 and deposited with the ATCC under Accession Number HB 8704.

2. A monoclonal antibody produced by the hybridoma cell line of claim 1.

3. A monoclonal antibody of claim 2 labeled with a detectable moiety.

4. A method of detecting a pigmentation associated antigen which weights about 70–80 kilodaltons and has an isoelectric point of about 5.2 to 5.6 comprising contacting a sample containing said antigen with the monoclonal antibody of claim 3 under conditions so as to form a complex between said antibody and said antigen and detecting the complex so formed, thereby detecting said antigen.

5. Method of claim 4, wherein said sample is normal cells or tissue.

6. Method as in claim 4, wherein said sample is cancerous cells or tissue.

7. Method as in claim 4, wherein said sample is melanin containing cells or tissue.

8. A method of diagnosing a melanoma which comprises contacting a sample from a subject with the monoclonal antibody of claim 3 under conditions so as to form a complex between the monoclonal antibody and an antigen derived from the melanoma and detecting the complex so formed, thereby diagnosing melanoma in the subject.

9. A method of claim 8 wherein the antigen is a pigmentation associated antigen weighing about 70–80 kilodaltons and having an isoelectric point of about 5.2 to 5.6.

* * * * *